United States Patent
Lee et al.

(10) Patent No.: US 9,782,371 B2
(45) Date of Patent: Oct. 10, 2017

(54) COMPOSITION FOR PROMOTING REMYELINATION IN NERVE CELLS COMPRISING 2,5-DIHYDROXYBENZENESULFONIC ACID AND USE THEREOF

(71) Applicants: Samsung Electronics Co., Ltd., Suwon-si, Gyeonggi-do (KR); Korea University Research and Business Foundation, Seoul (KR)

(72) Inventors: Yunil Lee, Yongin-si (KR); Suhyun Kim, Ansan-si (KR); Haechul Park, Ansan-si (KR); Sangchul Park, Seongnam-si (KR)

(73) Assignees: SAMSUNG ELECTRONICS CO., LTD., Suwon-si (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 15/202,341

(22) Filed: Jul. 5, 2016

(65) Prior Publication Data

US 2017/0049730 A1 Feb. 23, 2017

(30) Foreign Application Priority Data

Aug. 21, 2015 (KR) .......................... 10-2015-0118267

(51) Int. Cl.
*A61K 31/635* (2006.01)
*A61K 31/145* (2006.01)
(Continued)

(52) U.S. Cl.
CPC .................................. *A61K 31/185* (2013.01)

(58) Field of Classification Search
CPC ... A61K 31/145; A61K 31/167; A61K 31/635
See application file for complete search history.

(56) References Cited

U.S. PATENT DOCUMENTS 7,649,017 B2  1/2010  Fontes et al.
8,497,257 B2 * 7/2013  Cuevas Sanchez .. A61K 31/185
                                                            514/163

(Continued)

FOREIGN PATENT DOCUMENTS

JP   2005-537264 A  12/2005
KR   2010-0113505 A  10/2010

OTHER PUBLICATIONS

Notterpek et al., "Upregulation of the Endosomal-Lysosomal Pathway in the Trembler—J Neuropathy", *The Journal of Neuroscience*, 17(11): 4190-4200 (1997).

(Continued)

*Primary Examiner* — San-Ming Hui
(74) *Attorney, Agent, or Firm* — Leydig, Voit & Mayer, Ltd.

(57) ABSTRACT

A method of preventing or treating a disease associated with demyelination of a nerve cell in a mammal, a method of promoting remyelination or suppressing demyelination of a nerve cell in a mammal, and a method of reducing expression of PMP22 in a nerve cell of a mammal by administration of 2,5-dihydroxybenzenesulfonic acid or a pharmaceutically acceptable salt or solvate thereof.

7 Claims, 7 Drawing Sheets

(51) Int. Cl.
*A61K 31/167* (2006.01)
*A61K 31/185* (2006.01)

(56) References Cited

U.S. PATENT DOCUMENTS

| | | | |
|---|---|---|---|
| 2007/0010581 A1* | 1/2007 | Esteve-Soler | A61K 31/185 514/553 |
| 2010/0267756 A1 | 10/2010 | Arzamastsev et al. | |
| 2014/0080787 A1 | 3/2014 | Inglese et al. | |

OTHER PUBLICATIONS

Fang et al., A novel model of demyelination and remyelination in a GFP-transgenic zebrafish, *Biology Open*, 4(1): 62-68 (2015).
Kim et al., Promotion of Remyelination by Sulfasalazine in a Transgenic Zebrafish Model of Demyelination, *Molecules and Cells*, 38(11):1013-1021 (2015).
Mathis et al., Therapeutic options in Charcot-Marie-Tooth diseases, *Expert Review of Neurotherapeutics*, 15(4): 355-366 (2015).
European Patent Office, Extended Search Report for Application No. 16183584.8, dated Jan. 23, 2017, 6 pages.

* cited by examiner

COMPOSITION FOR PROMOTING REMYELINATION IN NERVE CELLS COMPRISING 2,5-DIHYDROXYBENZENESULFONIC ACID AND USE THEREOF

CROSS-REFERENCE TO RELATED APPLICATION

This application claims the benefit of Korean Patent Application No. 10-2015-0118267, filed on Aug. 21, 2015, in the Korean Intellectual Property Office, the disclosure of which is incorporated herein in its entirety by reference.

BACKGROUND

1. Field

The present disclosure relates to a composition for preventing or treating a disease associated with demyelination of nerve cells in a mammal, a composition for promoting remyelination or suppressing demyelination of nerve cells in a mammal, a composition for reducing expression of PMP22 in nerve cells of a mammal, a method of preventing or treating a disease associated with demyelination of nerve cells in a mammal, a method of promoting remyelination or suppressing demyelination of nerve cells in a mammal, and a method of reducing expression of PMP22 in nerve cells of a mammal.

2. Description of the Related Art

Demyelinating diseases are diseases of the nervous system in which the myelin sheaths of neurons are damaged. This damage impairs the conduction of signals in the affected nerves, which sequentially causes deficiency in sensation, movement, cognition, or other functions depending on which nerves are affected. Demyelinating diseases may include diseases affecting the central nervous system and peripheral nervous system. Demyelinating diseases of the peripheral nervous system include Guillain-Barre Syndrome and Charcot Marie Tooth (CMT) diseases. Demyelinating diseases of the central nervous system include multiple sclerosis. Ascorbic acid has been shown to be effective against peripheral nerve disease in animal models; however, this compound fails in clinical tests. Therefore, there is a need for a drug for the fundamental treatment of demyelinating diseases.

SUMMARY

Provided is a composition for preventing or treating a disease associated with demyelination of nerve cells in a mammal, the composition comprising 2,5-dihydroxybenzenesulfonic acid, or a pharmaceutically acceptable salt or solvate thereof.

Provided is a composition for promoting remyelination or suppressing demyelination of nerve cells in a mammal, the composition comprising 2,5-dihydroxybenzenesulfonic acid, or a pharmaceutically acceptable salt or solvate thereof.

Provided is a composition for reducing expression of peripheral myelin protein 22 (PMP22) in nerve cells of a mammal, the composition comprising 2,5-dihydroxybenzenesulfonic acid, or a pharmaceutically acceptable salt or solvate thereof.

Provided is a method of preventing or treating a disease associated with demyelination of a nerve cell in a mammal, the method comprising administering an effective amount of 2,5-dihydroxybenzenesulfonic acid or a pharmaceutically acceptable salt or solvate thereof into the mammal to thereby prevent or treat a disease associated with demyelination of the nerve cell of the mammal.

Provided is a method of promoting remyelination or suppressing demyelination of a nerve cell in a mammal, the method comprising administering an effective amount of 2,5-dihydroxybenzenesulfonic acid or a pharmaceutically acceptable salt or solvate thereof into the mammal to thereby promote remyelination or suppress demyelination in the nerve cell of the mammal.

Provided is a method of reducing expression of PMP22 in a nerve cell of a mammal, the method comprising administering an effective amount of 2,5-dihydroxybenzenesulfonic acid or a pharmaceutically acceptable salt or solvate thereof into a mammal to thereby reduce expression of PMP22 in the nerve cell of the mammal.

Additional aspects will be set forth in part in the description which follows and, in part, will be apparent from the description, or may be learned by practice of the presented exemplary embodiments.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
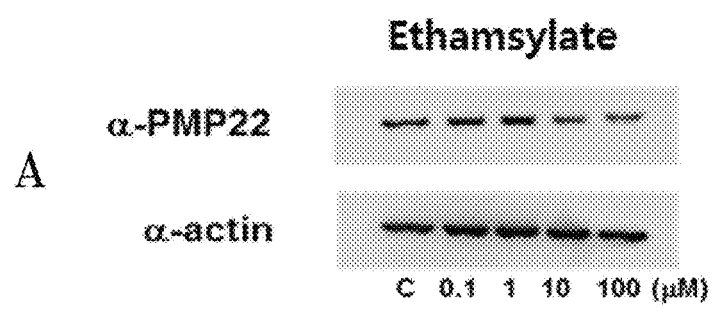
FIG. 1 illustrates the results of PMP22 gene expression analysis by Western blotting of rat Schwann cells including PMP22 overexpressed in the presence of ethamsylate (ES) at varied concentrations (panel A) and exposure times (panel B)
Figure 1:
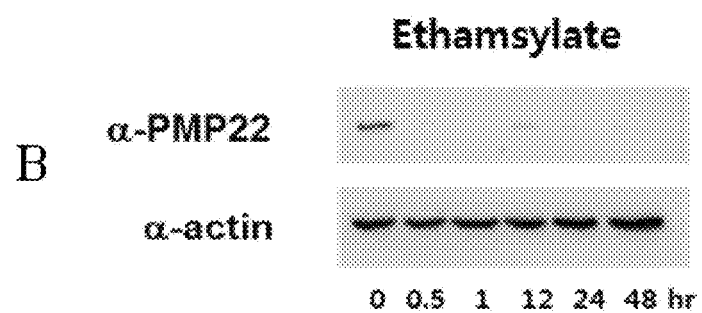

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

According to a first aspect of the present disclosure, there is provided a composition for preventing or treating a disease associated with demyelination of nerve cells in a mammal, the composition including 2,5-dihydroxybenzenesulfonic acid, or a pharmaceutically acceptable salt or solvate thereof.

According to a second aspect of the present disclosure, there is provided a composition for promoting remyelination or suppressing demyelination of nerve cells in a mammal, the composition including 2,5-dihydroxybenzenesulfonic acid, or a pharmaceutically acceptable salt or solvate thereof.

According to a third aspect of the present disclosure, there is provided a composition for reducing expression of peripheral myelin protein 22 (PMP22) in nerve cells of a mammal, the composition including 2,5-dihydroxybenzenesulfonic acid, or a pharmaceutically acceptable salt or solvate thereof.

In the compositions according to the first, second, and third aspects of the present disclosure, the 2,5-dihydroxybenzenesulfonic acid may be in the form of a pharmaceutically acceptable salt thereof. Examples of the pharmaceutically acceptable salt may include acid addition salts that are commonly used in the pharmaceutical field, for example, salts derived from inorganic acids such as hydrochloric acid, hydrobromic acid, sulfuric acid, sulfamic acid, phosphoric acid, or nitric acid; and salts derived from organic acids such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxy-benzoic acid, fumaric acid, toluenesulfonic acid, oxalic acid, or trifluoroacetic acid. Examples of the pharmaceutically acceptable salt may include base addition salts, for example, salts derived from bases such as ammonium, dimethylamine, monomethylamine, monoethylamine, or diethylamine. Examples of the pharmaceutically acceptable salt may include common metal salts, for example, salts derived from metals such as lithium, sodium, potassium, magnesium, or calcium. The above-listed acid addition salts, base addition salts, and metal salts may be prepared according to a common method in the art. For example, a base addition salt or a metal salt may be obtained by reacting an ionic form of 2,5-dihydroxybenzenesulfonic acid, i.e., 2,5-dihydroxybenzene sulfonate, with an appropriate base (for example, diethylamine) or metal ion (for example, calcium, magnesium, or sodium ion). For example, the resulting base addition salt may be 2,5-dihydroxybenzene sulfonate diethylammonium salt (hereinafter, "ethamsylate").

A pharmaceutically acceptable salt of 2,5-dihydroxybenzenesulfonic acid may have a structure of Formula 1.

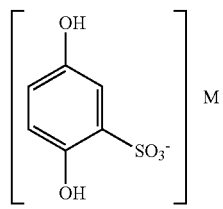

(Formula 1)

In Formula 1, M may be $[NH_{4-x}R_x]^+$, wherein x may be 0, 1, 2, 3, or 4; and when x>1, R(s) may be the same as or differ from each other, for example, may be a branched or unbranched $C_{1-4}$-alkyl-radical.

The 2,5-dihydroxybenzenesulfonic acid may be in the form of a solvate thereof. The term "solvate" refers a complex or aggregate that consists of or comprises at least one solute molecule, that is, a compound represented by Formula 1 or a pharmaceutically acceptable salt of the compound; and at least one solvent molecule. The solvate may be, for example, a complex or aggregate formed with water, methanol, ethanol, isopropanol, or acetic acid.

The 2,5-dihydroxybenzenesulfonic acid may be in the form of a stereoisomer of the compound thereof. Examples of the stereoisomer include all types of stereoisomers such as enantiomers and diastereomers. The 2,5-dihydroxybenzenesulfonic acid compound may be in a stereoisomerically pure form of a stereoisomer or a mixture of at least two stereoisomers, for example, a racemic mixture. Isolation of a specific stereoisomer may be performed by using one of the known methods in the art.

The 2,5-dihydroxybenzenesulfonic acid may be chemically synthesized or commercially purchasable.

In the first, second, and third aspects of the present disclosure, the composition may be a pharmaceutical composition. The composition may further include a pharmaceutically acceptable carrier. The term "pharmaceutically acceptable carrier" as used herein denotes a material that is used in combination with an active ingredient, that is, generally, an inert material, to help application of the active ingredient. Examples of the pharmaceutically acceptable carrier may include, in general, a pharmaceutically acceptable excipient, additive, or diluent. Examples of the pharmaceutically acceptable carrier may include at least one selected from the group consisting of a filler, a binder, a disintegrant, a buffer, a preservative, an antioxidant, a lubricant, a flavoring agent, a thickener, a coloring agent, an emulsifier, a suspending agent, a stabilizer, and an isotonic agent.

The composition may include 2,5-dihydroxybenzenesulfonic acid or a pharmaceutically acceptable salt or solvate thereof, at a "therapeutically effective amount". In the composition, the term "therapeutically effective amount" as used herein refers to a sufficient amount that produces a therapeutic effect when administered to a subject in need of treatment. The term "treatment" as used herein refers to treatment of a disease or medical condition, for example, a disease associated with demyelination of a subject such as a mammal, including humans, and the meaning of treatment is: (a) ameliorating the disease or medical condition such as by eliminating or causing regression of the disease or medical condition of a patient; (b) suppressing the disease or medical condition such as by slowing or arresting the development of the disease or medical condition of a patient; or (c) alleviating a symptom of the disease or medical condition of a patient to any degree. The composition also may be used for the preventative (Prophylactic) treatment of a disease or medical condition.

The composition may include an "effective amount of 2,5-dihydroxybenzenesulfonic acid or a pharmaceutically acceptable salt or solvate thereof for promoting remyelination of a nerve cell in a mammal" or "an effective amount of 2,5-dihydroxybenzenesulfonic acid or a pharmaceutically acceptable salt or solvate thereof for reducing expression of PMP22 in a nerve cell of a mammal". The "effective amount" may be appropriately selected by one of ordinary skill in the art. For example, the "effective amount" may be in a range of about 0.01 mg to about 10,000 mg, 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg.

The composition may include 2,5-dihydroxybenzenesulfonic acid or a pharmaceutically acceptable salt or solvate thereof as an active ingredient. The term "active ingredient" refers to an ingredient enabling a function of the composition as described above, but excludes the case where the amount of the active ingredient is so small to act like impurities.

The composition may be prepared for oral administration or parenteral administration including intravenous, intraperitoneal, subcutaneous, rectal, and topical administration. Thus, the composition may be formulated into various forms such as tablets, capsules, aqueous solutions, or suspensions. In the case of tablets for oral administration, an excipient such as lactose or corn starch and a lubricant such as magnesium stearate may be added thereto in general. In the case of capsules for oral administration, lactose and/or dried corn starch may be used as a diluent. When an aqueous suspending agent for oral administration is needed, active ingredients may be attached to an emulsifier and/or a suspending agent. If necessary, a predetermined sweetening agent and/or a flavoring agent may be added to the composition. For intraneural, intramuscular, intraperitoneal, subcutaneous, and intravenous administration, a sterilized solution of the active ingredients is generally prepared, wherein the pH of the sterilized solution needs to be appropriately adjusted and buffered. For intravenous administration, the total concentration of solutes needs to be controlled to render the formulated composition isotonic. The composition may be formulated into an aqueous solution including a pharmaceutically acceptable carrier such as salt water at a pH of 7.4. The aqueous solution may be administered to intramuscular or intraneural blood flow of a patient by local bolus injection.

2,5-dihydroxybenzenesulfonic acid or a pharmaceutically acceptable salt or solvate thereof may suppress demyelination or recover demyelinated neurons by remyelinating neurons.

The composition may be used in combination with at least one other treatment agent for treating a disease associated with demyelination. Alternatively, the composition may include 2,5-dihydroxybenzenesulfonic acid or a pharmaceutically acceptable salt or solvate thereof without any other active ingredient for treating a disease associated with demyelination.

The composition may be used to treat a disease associated with demyelination in nerve cells of a mammal. The disease associated with demyelination of neurons (hereinafter, also referred to as "demyelinating disease") refers to a nervous system disease with damaged myelin sheaths of neurons. The damage of myelin sheaths of neurons may include any damage reducing signal conduction in neurons, including separation of myelin bound to neurons, or amount reduction or structural deformation of myelin. This damage impairs the conduction of signals in the affected nerves, which, in turn, causes deficiency in sensation, movement, cognition, or other functions depending on which nerves are involved. The disease may include diseases affecting the central nervous system (referred to also as "central nervous system demyelinating diseases") and peripheral nervous system (referred to also as "peripheral nervous system demyelinating diseases"). The central nervous system demyelinating diseases may include: multiple sclerosis; Devic's disease; inflammatory demyelinating diseases; central nervous system neuropathies such as those caused by Vitamin B12 deficiency; myelopathies such as Tabes dorsalis; leukoencephalopathies such as progressive multifocal leukoencephalopathy; leukodystrophies; Guillain-Barre Syndrome; and chronic inflammatory demyelinating polyneuropathy, which is a chronic counterpart of Guillain-Barre Syndrome; or a combination thereof. The peripheral nervous system demyelinating diseases may include anti-MAG peripheral neuropathy, Charcot Marie Tooth (CMT) disease, copper deficiency, progressive inflammatory neuropathy, or a combination thereof. For example, the disease associated with demyelination of a neuron may be multiple sclerosis, Guillain-Barre Syndrome, CMT disease, or a combination thereof. The CMT disease may be a CMT1A sub-type, a CMT1E sub-type, or a CMT3 sub-type.

In some embodiments of the composition, the disease associated with demyelination of neurons may be caused from overexpression of PMP22. PMP22 is a protein which is encoded in humans by the PMP22 gene. The integral membrane protein encoded by this gene is a hydrophobic tetraspan glycoprotein expressed mainly in Schwann cells and is a major component of compact myelin in the peripheral nervous system. Although PMP22 is a major component of compact myelin in the peripheral nervous system, the composition according to an embodiment as described above may be effective on not only the nerve cells of the peripheral nervous system but also the nerve cells of the central nervous system. PMP22 is known to interact with myelin protein zero. Various mutations of the gene are causes of CMT1A, Dejerine-Scottas disease, and hereditary neuropathy with liability to pressure palsy (HNPP). CMT1A is the most common form of the disease, which at least 60% of all CMT patients belong to. CMT1A is caused by a duplication of the PMP22 gene on Chromosome 17. This CMT disease may be caused from not only having two copies of the gene, but also having three copies of the gene, including two copies on a chromosome and one copy on another chromosome.

In some embodiments of the composition, the mammal may be a human. The mammal may have demyelinated neurons and/or a disease associated with demyelination.

In some embodiments of the composition, the overexpression of PMP22 in the nerve cell may be in progress or in completion. The nerve cell may be in progress or completion of demyelination caused from overexpression of PMP22. The nerve cell may be in the peripheral nervous system and/or the central nervous system. The nerve cell may be present or may live in vivo or in vitro.

According to another aspect of the present disclosure, there is provided a composition for preventing or treating a disease associated with overexpression of PMP22 in a nerve cell of a mammal, the composition including 2,5-dihydroxybenzenesulfonic acid, or a pharmaceutically acceptable salt or solvate thereof. As used herein, the "overexpression of PMP22" refers to increased expression of PMP22 compared to normal nerve cells without damage in myelin sheaths (e.g., nerve cells of a normal, healthy patient). The expression of PMP22 may be measured at either the mRNA level or protein level. The mRNA level may measured by using RNA isolation, nucleic acid amplification method such polymerase chain reaction including RT-PCR etc. The protein level may be measured by isolation the protein using chromatography such ion exchange, size exclusion, affinity chromatography etc., filtration, salting out. The protein level may be measured by using a detection method. For example, a detection method using an antibody specific a PMP22 such as enzyme linked immunosorbent assay may be used. The "overexpression of PMP22" refers to increased expression of PMP22 compared to normal nerve cells, for example, by 5% or more, 10% or more, 50% or more, 100% or more, 5% to 100%, 10% to 100%, 20% to 100%, 5% to 80%, 5% to 50%, 10% to 50% increased expression.

According to another aspect of the present disclosure, there is provided use of 2,5-dihydroxybenzenesulfonic acid defined above, or a pharmaceutically acceptable salt or solvate thereof in treating a disease associated with demyelination.

According to another aspect of the present disclosure, there is provided use of 2,5-dihydroxybenzenesulfonic acid defined above or a pharmaceutically acceptable salt or solvate thereof in preparing a medication for treating a disease associated with demyelination.

According to a fourth aspect of the present disclosure, there is provided a method of preventing or treating a disease associated with demyelination in a nerve cell of a mammal, the method including administering an effective amount of 2,5-dihydroxybenzenesulfonic acid or a pharmaceutically acceptable salt or solvate thereof into the mammal to thereby prevent or treat a disease associated with demyelination of the nerve cell of the mammal.

According to a fifth aspect of the present disclosure, there is provided a method of promoting remyelination or suppressing demyelination in a nerve cell of a mammal, the method including administering an effective amount of 2,5-dihydroxybenzenesulfonic acid or a pharmaceutically acceptable salt or solvate thereof into the mammal to thereby promote remyelination or suppress demyelination in the nerve cell of the mammal.

According to a sixth aspect of the present disclosure, there is provided a method of reducing expression of PMP22 in a nerve cell of a mammal, the method including administering an effective amount of 2,5-dihydroxybenzenesulfonic acid or a pharmaceutically acceptable salt or solvate thereof into the mammal to thereby reduce expression of PMP22 in the nerve cell of the mammal.

In the fourth, fifth, and six aspects of the present disclosure, unless otherwise defined, the same terms as those used in connection with the first, second, and third aspects of the present disclosure are understood as having the same meaning as described in the first, second, and third aspects.

In the fourth aspect of the present disclosure, the demyelination may occur in a nerve cell of the central nervous system or peripheral nervous system. The demyelination may be caused from overexpression of PMP22. The disease associated with demyelination in a nerve cell of a mammal may be CMT disease, Dejerine-Sottas disease, hereditary neuropathy with liability to pressure palsy (HNPP), multiple sclerosis, or Guillain-Barre In the fifth aspect of the present disclosure, a disease associated with demyelination may be treated by the promotion of remyelination or the suppression of demyelination in a nerve cell of a mammal. The nerve cell may be in progress or completion of demyelination caused from overexpression of PMP22. The demyelination may occur in a nerve cell of the central nervous system or peripheral nervous system.

In the sixth aspect of the present disclosure, a disease associated with demyelination may be treated by the reduction in expression of PMP22 in a nerve cell of a mammal. The nerve cell may be in progress or completion of demyelination caused from overexpression of PMP22. The demyelination may occur in a nerve cell of the central nervous system or peripheral nervous system.

In the methods according to the fourth, fifth, and sixth aspects of the present disclosure, a route of the administration may be appropriately selected by one of ordinary skill in the art. For example, the route of the administration may be oral, parenteral, or local or topical administration. The local administration may be administration to a nervous system, for example, the brain.

An administration amount may vary depending on the condition of a patient, an administration route, and a doctor's decision. An effective administration amount may be obtained based on a dose-response curve obtained through an in vitro or animal model test. A ratio and/or concentration of the compound, i.e., 2,5-dihydroxybenzenesulfonic acid or a pharmaceutically acceptable salt or solvate thereof in a composition according to any of the above-described embodiments may be determined depending on chemical characteristics, an administration route, and a therapeutic administration amount. An amount of administration to a subject may be an effective amount of, for example, about 1 µg/kg to about 1 g/kg per day, or about 0.1 mg/kg to about 500 mg/kg per day. The amount may vary depending on an age, weight, sensitiveness, or symptoms of the subject.

In the fourth, fifth, and sixth aspects of the present disclosure, the method may further include collecting related information about demyelination of a nerve cell in the subject before the administration. The related information about the demyelination may include a demyelination level, a demyelination rate, a demyelination type, and the like. The related information about the demyelination may be obtained by observing the nerve cell with an optical or fluorescent microscope or by using a myelin sheath-specific marker. Accordingly, in the fourth, fifth, and sixth aspects of the present disclosure, the method may further include measuring demyelination of a nerve cell. The nerve cell may originate from a subject who is suspected of having a disease associated with demyelination, or potentially having the disease. The method may also further include determining whether demyelination is in progress or completion faster than in a control group, based on the collected related information about demyelination. The control group may have a myelination level that is similar to that of normal nerve cells originating from a subject without demyelinating disease or to that of normal nerve cells of a normal subject. The method may include administering 2,5-dihydroxybenzenesulfonic acid, or a pharmaceutically acceptable salt or solvate thereof to a subject, i.e., a mammal that is determined to be in progress or completion of demyelination more than in the control group in the determination step.

In the fourth, fifth, and sixth aspects of the present disclosure, the method may further include measuring an expression level of PMP22 in the subject or a nerve cell of the subject before the administration. The expression level of PMP22 may be measured at either the mRNA level or protein level. The expression level of PMP22 may be measured by amplification (for example, a polymerization chain reaction (PCR)), Southern blotting, or sequence analysis using an mRNA-specific primer nucleotide, or by separation of a PMP22 expression protein, Western blotting, or the like. The nerve cell may originate from a subject having a disease associated with demyelination or potentially having a risk of the disease. The method may further include determining whether a measured expression level of PMP22 obtained in the measurement step is higher than an expression level in a control group. The control group may have a myelination level that is similar to that of normal nerve cells originating from a subject without demyelinating disease or to that of normal nerve cells of a normal, healthy subject. The method may include administering 2,5-dihydroxybenzenesulfonic acid, or a pharmaceutically acceptable salt or solvate thereof to a subject, i.e., a mammal that is determined to have a higher expression level of PMP22 than that in the control group in the determination step. The higher expression level of PMP22 may be at least about 1%, about 5%, about 10%, about 20%, about 50%, about 100%, about 200%, about 500%, about 1000%, about 1 to about 1000%, about 5 to about 1000%, about 10 to about 1000%, about 20 to about 1000%, about 50 to about 1000%, about 100 to about 1000%, about 200 to about 1000%, or about 500 to about 1000% higher than the control.

According to another aspect of the present disclosure, there is provided a method of promoting remyelination or suppressing demyelination in a nerve cell of a mammal, the method including contacting the nerve cell of the mammal with an effective amount of 2,5-dihydroxybenzenesulfonic acid or a pharmaceutically acceptable salt or solvate thereof to thereby promote remyelination or suppress demyelination in the nerve cell of the mammal. The nerve cell may be a nerve cell separated from a subject or a nerve cell that lives in vitro.

According to another aspect of the present disclosure, there is provided a method of reducing expression of PMP22 in a nerve cell of a mammal, the method comprises contacting the nerve cell of the mammal with an effective amount of 2,5-dihydroxybenzenesulfonic acid or a pharmaceutically acceptable salt or solvate thereof to thereby reduce expression of PMP22 in the nerve cell of the mammal. The nerve cell may be a nerve cell separated from a subject or a nerve cell that lives in vitro.

In the methods according to the above-described aspects of the present disclosure, the contacting may be performed in a liquid medium, for example, in a culture medium of the nerve cell or a buffer.

One or more embodiments of the present disclosure will now be described in detail with reference to the following examples. However, these examples are only for illustrative purposes and are not intended to limit the scope of the one or more embodiments of the present disclosure.

EXAMPLE 1

Effect of Ethamsylate on Remyelination in Nerve Cells (1) Effect of Ethamsylate on PMP22 Expression in Nerve Cells Rat Schwann cells were inoculated at a concentration of about $10^5$ cells/mL into each well of a 12-well plate including 2 mL of a Dulbecco's Modified Eagle's Medium (DMEM) containing 10% fetal bovine serum (FBS), 100 units/mL of penicillin, and 100 units/mL of streptomycin, and incubated in a 5%-$CO_2$ incubator at about 37° C. to a cell density of about 60% to about 65%. Then, ethamsylate (diethyl ammonium 2,5-dihydroxybenzene sulfonic acid ("ES"), available from Selleckchem, Tex.) was added to the wells at different concentrations, followed by incubation under the same conditions for about 24 hours. Rat Schwann cells are often used in in vitro models for neuronal function and differentiation. The rat Schwann cells used herein were modified to consistently overexpress the human PMP22 gene by lentivital mediated integration of PMP22 into a chromosome and selective use of puromycin-resistant markers, thereby constructing a new rat Schwann PMP22 cell model. The rat Schwann cells (ATCC number; CRL-2768) were purchased from the American Type Culture Collection (ATCC).

After 2 mL of the culture medium was removed, the resulting rat Schwann cells were washed with phosphate buffered saline (PBS), followed by adding a lysis solution containing a 0.5% triton X-100 in PBS thereto, collecting the cells using a scraper, leaving the cells on ice for about 30 minutes, and then disrupting the cells. Using a bicinchoninic acid (BCA) protein assay, the amount of protein in each sample was normalized to 1 ug/uL, followed by sodium dodecyl sulfate polyacrylamide gel electrophoresis (SDS-PAGE, Invitrogen) and Western blotting with rabbit anti-PMP22 (Novus biological) and rabbit anti-actin (Sigma) primary antibodies and horseradish peroxidase (HRP)-conjugated anti-rabbit secondary antibody.

FIG. 1 illustrates the results of PMP22 gene expression analysis by Western blotting of rat Schwann cells including PMP22 overexpressed in the presence of ethamsylate. In FIG. 1, A and B are both Western blotting images, wherein panel A shows PMP22 protein expression in cells treated with 0.1 µM, 1 µM, 10 µM, and 100 µM of ethamsylate in dimethyl sulfoxide (DMSO) for about 24 hours. In panel A of FIG. 1, "C" indicates a control group including DMSO as a solvent instead of ethamsylate. The experiment was repeated 4 times (n=4). Panel B of FIG. 1 shows PMP22 protein expression in cells treated with 10 µM of ethamsylate for 0, 0.5, 1, 12, 24, and 48 hours, wherein "0 hour" indicates a control group to which ethamsylate was not added.

As shown in panel A of FIG. 1, increased concentrations of ethamsylate led to a decrease in the amount of PMP22 protein expressed. It was also found that the expression level of PMP22 protein after incubation for 0.5, 1, 12, 24, and 48 hours in a culture medium containing 10 µM of ethamsylate was decreased compared to the control group (panel B in FIG. 1).

(2) Effect of Ethamsylate on PMP22 Expression In Vivo

Transformed Zebrafish (Danio rerio) in which genes respectively encoding an Mbp:EGFP fusion protein and a Claudink:EGFP fusion protein that are specifically expressed in myelin and emit fluorescence by using promoters of a myelin basic protein (MBP) gene and a Claudink gene were prepared, by transforming Zebrafish cells with genes respectively encoding an Mbp:EGFP fusion protein and a Claudink:EGFP fusion protein. Specifically, the NfsB virulence gene encodes a nitroreductase (NTR) enzyme. NTRs do not cause any cytotoxicity in typical zebrafish. However, when metronidazole (MTZ) is added to cells, the cells convert MTZ into a cytotoxic material by using NTR, which induces apoptosis. Genetically engineered zebrafish, i.e., transformed zebrafish that express the NfsB virulence gene specifically in differentiated oligodendrocytes and Schwann cells were prepared by using promoters of mbp and claudink genes that specifically operate in differentiated myelin to express myelin-specific genes bound to myelin, and using the Gal4-UAS transactivator system. Next, it was confirmed that the NfsB virulence gene was myelin-specifically expressed in the transformed zebrafish.

When the MTZ substrate was added to a culture medium of the transformed zebrafish that express the nfsB virulence gene specifically in oligodendrocytes and Schwann cells, it was found that apoptosis was induced in the oligodendrocytes and Schwann cells of the transformed zebrafish in which the promoters of mbp and claudink genes specifically operate, and demyelination was consequentially induced. As a result, an animal model of demyelination that is induced in the presence of MTZ was established. Hereinafter, this animal model is also referred to as zebrafish (Mbp (or claudink):gal4::UAS:nfsB (NTR, toxin)::UAS:gfp). After removing the added MTZ substrate from the culture medium, the transformed zebrafish were then cultured in a culture medium free of MTZ for 1 day, followed by a recovery period. This study, described in greater detail below, confirmed that natural remyelination occurred in the demyelinated central nervous system and peripheral nervous system and that ES drug has an effect of promoting remyelination.

Figure 2:
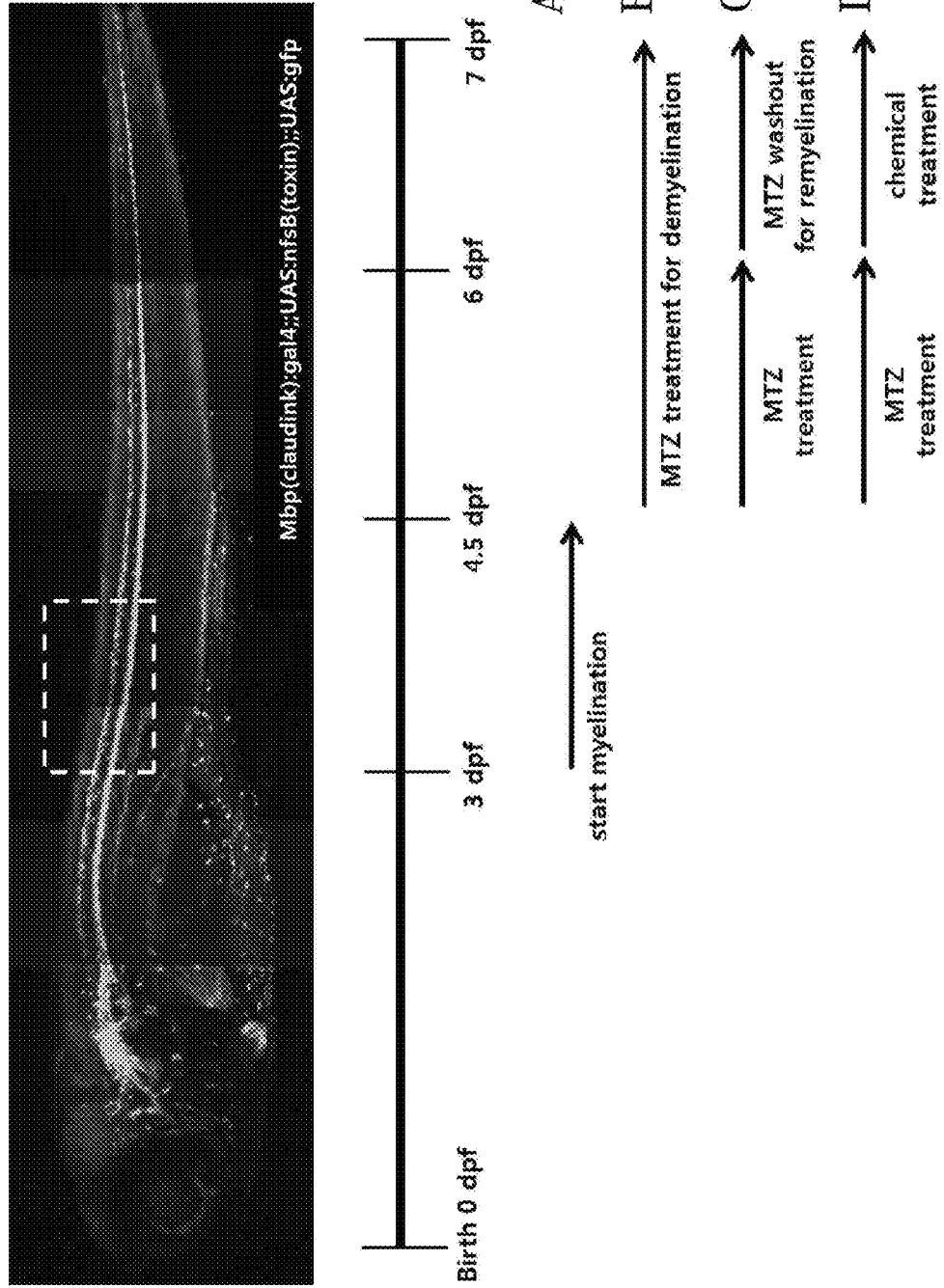
FIG. 2 provides a microscopic image of zebrafish (Mbp: gal4::UAS:nfsB (NTR, toxin)::UAS:gfp) obtained using a confocal laser microscope, and schematic illustration of experimental procedures for myelination, demyelination, and remyelination (panels A-D)

100 zebrafish were incubated in egg water or an embryo medium (EM) (including 15 mM NaCl, 0.5 mM KCl, 1 mM $CaCl_2$, 1 mM $MgSO_4$, 0.15 mM $KH_2PO_4$, 0.05 mM $NH_2PO_4$, and 0.7 mM $NaHCO_3$) in a water bath at about 28.5° C. containing 1 L of water for 4.5 dpf (days post-fertilization) from the date of birth, and 10 mM of MTZ (Sigma) dissolved in an EM including 0.2% DMSO was then added thereto for 36 hours of demyelination. The zebrafish were moved to wells of a 96-well plate containing different drugs, and then incubated at about 28.5° C. (FIG. 2 panel B). Some of the zebrafish were allowed to be remyelinated by removing MTZ from the EM by washing the demyelinated zebrafish with a new EM three times after 6 dpf from the date of birth (FIG. 2 panel C). Another group of zebrafish was incubated under the same conditions as in panel C, except that 10 μM of ES was added (FIG. 2 panel D, wherein "chemical treatment" refers to ES treatment). A control group was incubated under the same conditions except that 0.2% of DMSO, instead of MTZ, was added.

FIG. 2 provides a microscopic image of zebrafish (Mbp:gal4::UAS:nfsB (NTR, toxin)::UAS:gfp) obtained using a confocal laser microscope. In the microscopic image of FIG. 2, a white dashed-line box delimits a region of myelin to monitor remyelination in the central nervous system and the peripheral nervous system. The central brightest region corresponds to the central nervous system, and a relatively dark region under the central nervous system region corresponds to the peripheral nervous system. In FIG. 2, panels A-D below the confocal laser microscopic image provide a schematic illustration of experimental processes, i.e., of myelination from 3 dpf from the date of birth (A), addition of MTZ at 4.5 dpf (B), washing out or removing MTZ at 6 dpf (hereinafter, also referred to as "Recovery 1 day") (C), and addition of 10 μM of ES (D). The experiment was performed till 7 dpf by a multiple of 18 (n=18). In FIG. 2, "Mbp(claudink)" in the indication of "Zebrafish (Mbp (claudink):gal4::UAS:nfsB (NTR, toxin)::UAS:gfp)" means that either "Mbp" or "claudink" promoter may be equally used in transformed zebrafish.

Figure 3:
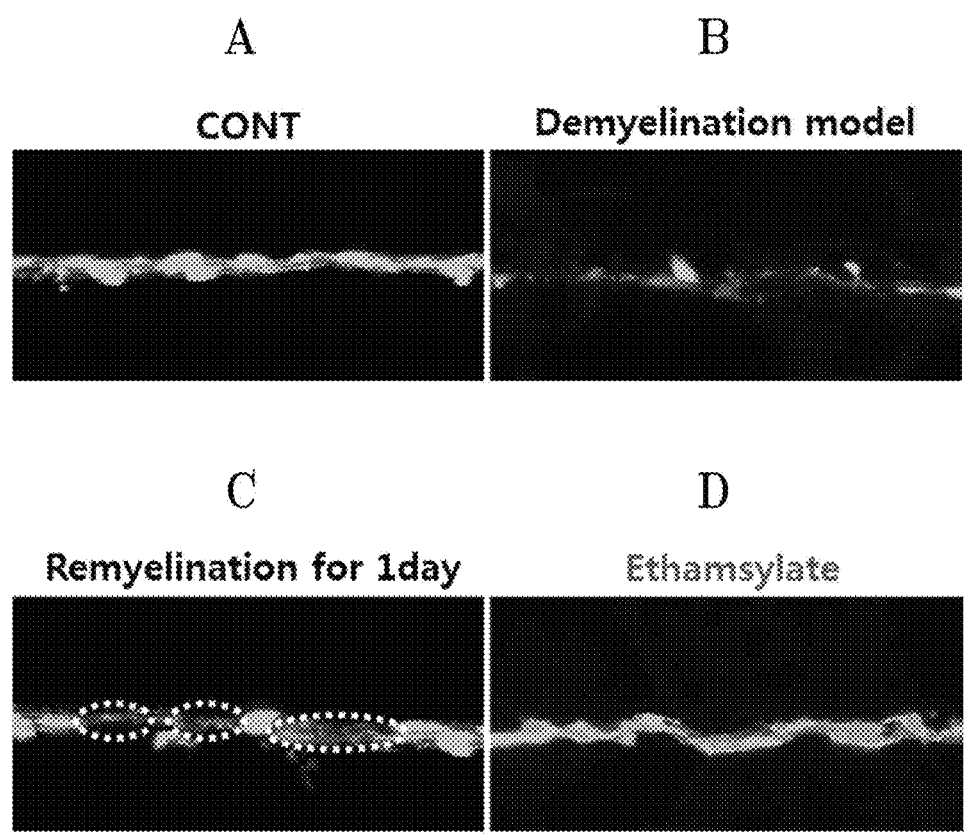
FIG. 3 illustrates the results of green fluorescent protein (GFP)-fluorescence microscopy using a confocal laser microscope on myelin surrounding axons of the posterior lateral line nerves (PLLs) of the zebrafish (Mbp:gal4::UAS: nfsB (NTR, toxin)::UAS:gfp) incubated under various conditions (panels A-D)

FIG. 3 illustrates the results of green fluorescent protein (GFP)-fluorescence microscopy using a confocal laser microscope on myelin surrounding axons of the posterior lateral line nerves (PLLs) of the zebrafish (Mbp:gal4::UAS:nfsB (NTR, toxin)::UAS:gfp) incubated under various conditions. FIG. 3, panels A, B, C, and D, illustrate the results of experiments performed as described above in connection with A, B, C, and D and the experimental processes in FIG. 2. When the zebrafish were incubated in the absence of MTZ and ethamsylate as in FIG. 3 panel A, sufficient myelin was present in the peripheral nervous system of the zebrafish (FIG. 3 panel A). When the zebrafish were cultured in the presence of MTZ from about 4.5 dpf to 7 dpf (for about 2.5 days), nearly no GFP fluorescence was observed, indicating that most myelin was removed (FIG. 3 panel B). When the zebrafish cultured in the presence of MTZ from 4.5 dpf to 6 dpf was further incubated from 6 dpf to 7 dpf (for about 1 day) in a medium to which no ES was added after removing MTZ from the medium by washing, myelin in the peripheral nervous system was still partially not myelinated (see white dashed-line regions in FIG. 3 panel C). On the other hand, when the zebrafish cultured in the presence of MTZ from 4.5 dpf to 6 dpf were further incubated from 6 dpf to 7 dpf (for about 1 day) in a medium to which ES was added after removing MTZ from the medium by washing, myelin in the peripheral nervous system was completely remyelinated so that GFP-originated green fluorescence was observed in the all the regions (FIG. 3 panel D). In FIG. 3, the intensity of green fluorescence is proportional to the degree of myelination.

Figure 4:
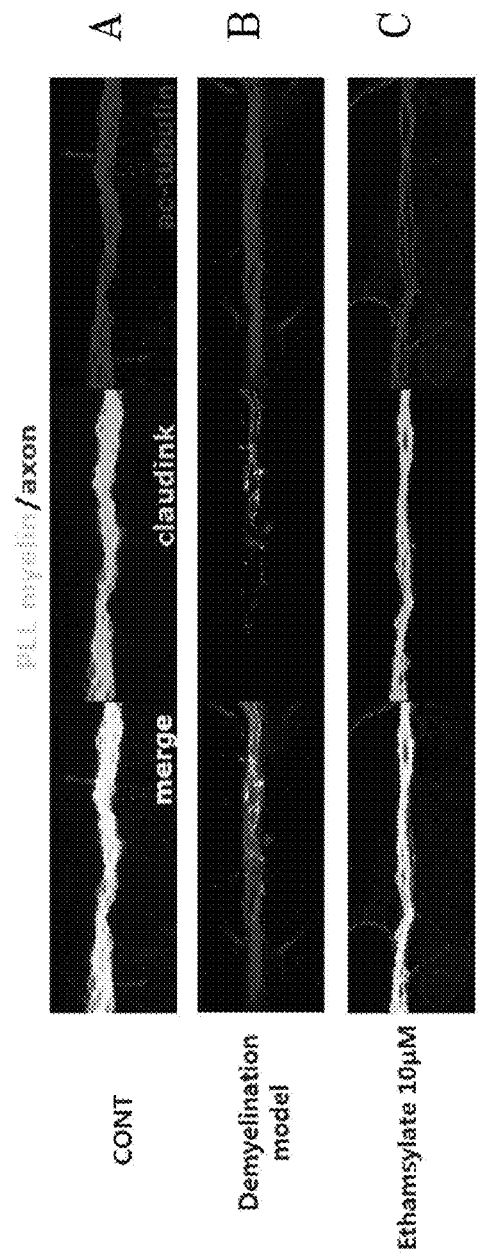
FIG. 4 illustrates the results of GFP-fluorescence (green) microscopy and immunofluorescence microscopy with staining of acetylated-tubulin (red fluorescence), using a confocal laser microscope on myelin of the peripheral nervous system of the zebrafish (Claudink:gal4::UAS:nfsB (NTR, toxin)::UAS:gfp) incubated under various conditions (panels A-C)

FIG. 4 illustrates the results of GFP-fluorescence (green) microscopy and immunofluorescence microscopy with staining of acetylated-tubulin (red fluorescence), using a confocal laser microscope on myelin of the peripheral nervous system of the zebrafish (Claudink:gal4::UAS:nfsB (NTR, toxin)::UAS:gfp) incubated under various conditions. Claudink promoters that more specifically operate on myelin than Mbp promoters may be used to more quantitatively observe demyelination and remyelination in nerve cells. In FIG. 4, "claudink" and "ac-tubulin" denote a green fluorescent image by GFP expressed specifically in myelin by the claudink promoter and a red fluorescent image with immunostaining of acetylated-tubulin expressed specifically in axons, respectively, and "merge" denotes a merged image of the two images. The immunostaining of acetylated-tubulin was performed using anti-mouse acetylated-tubulin primary antibody and Alexa647-conjugated anti-mouse secondary antibody to measure blue fluorescence, followed by blue to red conversion for high-contrast imaging to green fluorescence. Hereinafter, immunostaining of acetylated-tubulin is performed in the same manner as described here. In FIG. 4, "PLL myelin" indicates myelin surrounding axons of the PLLs. As shown in FIG. 4, ES was found to promote remyelination. FIG. 4 panels A, B, and C denote the same experimental processes as A, B, and D of FIG. 2, respectively, under the same conditions.

Figure 5:
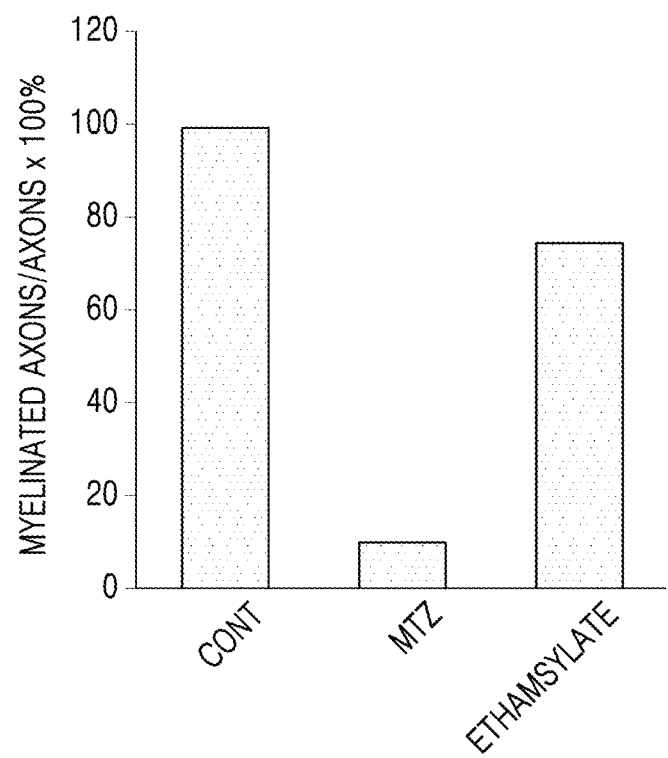
FIG. 5 illustrates a ratio of myelinated axons to total axons, obtained from the fluorescence intensities of the fluorescent images in FIG. 4.

FIG. 5 illustrates a ratio of myelinated axons to total axons, obtained from the fluorescence intensities of the fluorescent images in FIG. 4. In FIG. 5, "Cont", "MTZ", and "Ethamsylate" indicate the results from panels A, B, and C of FIG. 4, respectively. The ratio of myelinated axons to total axons is represented as a percentage ratio of the green fluorescence intensity of GFP expressed specifically in myelin by the claudink promoter to the red fluorescence intensity from the immunostaining by acetylated-tubulin expressed specifically in axons shown in FIG. 4.

As shown in FIGS. 4 and 5, the ratio of myelinated axons to total axons was significantly higher in the presence of ES than in the MTZ treated sample, indicating that ES promotes myelination in demyelinated nerve cells.

Figure 6:
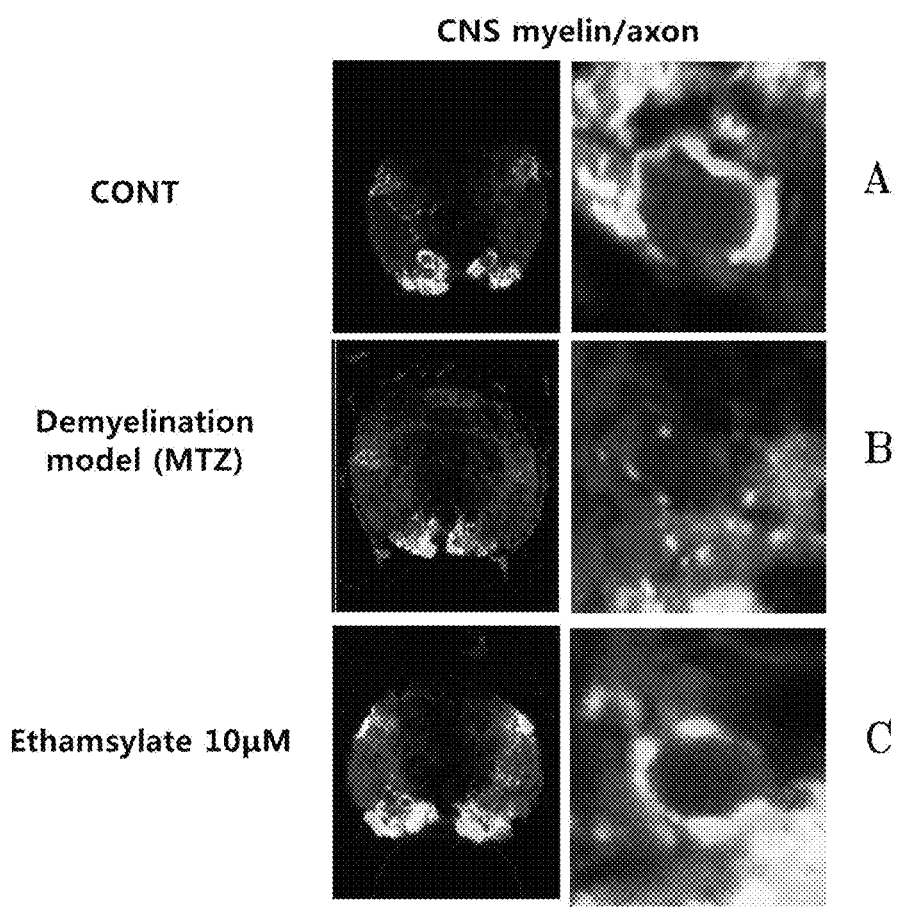
FIG. 6 illustrates the results of GFP-originated fluorescence microscopy and red fluorescence microscopy with immunostaining of acetylated-tubulin that is expressed specific to axons, using a confocal laser microscope on sections of Mauthner axons and myelin in the central nervous system of the zebrafish (ClaudinK:gal4::UAS:nfsB (NTR, toxin):: UAS:gfp) incubated under various conditions (panels A-C)

FIG. 6 illustrates the results of GFP-originated fluorescence microscopy and red fluorescence microscopy with immunostaining by acetylated-tubulin that is expressed specific to axons, by using a confocal laser microscope on sections of Mauthner axons and myelin in the central nervous system of the zebrafish (ClaudinK:gal4::UAS:nfsB (NTR, toxin)::UAS:gfp) incubated under various conditions. FIG. 6, panels A, B, and C indicate the results from the same experimental processes as panels A, B, and D in FIGS. 2 and 3, respectively, under the same conditions. In FIG. 6, panel A denotes a control group cultured in a medium including neither MTZ nor ES. The axon and fiber diameters were obtained by calculating the diameters from the intensities of GFP-originated fluorescence and red axonal fluorescence with the Image J program.

Figure 7:
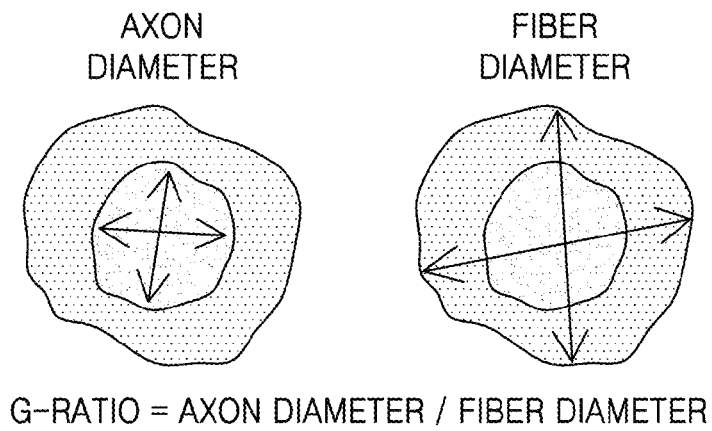
FIG. 7 is a schematic illustration of the definition of a g-ratio as a diameter ratio of axon to nerve fiber.

FIG. 7 is a schematic illustration of the definition of a g-ratio as a diameter ratio of axon to nerve fiber.

Figure 8:
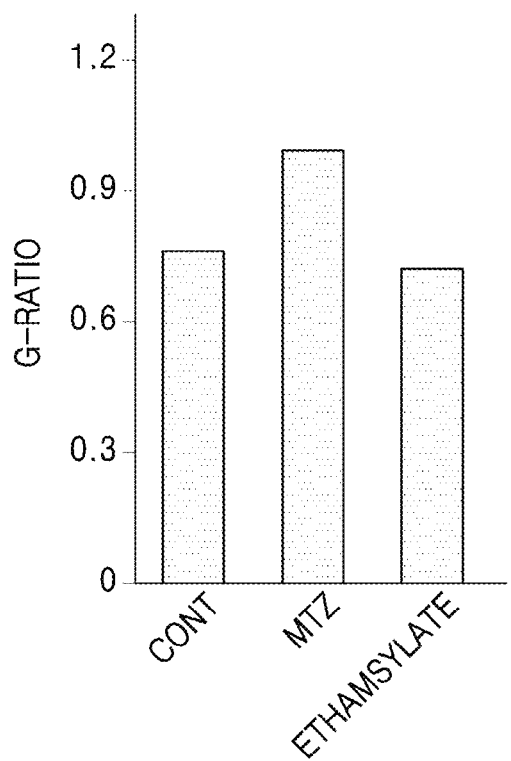
FIG. 8 is a graph of the g-ratio obtained from the results of FIG. 6.

FIG. 8 is a graph of g-ratio obtained from the results of FIG. 6. In FIG. 8, "Cont", "MTZ", and "Ethamsylate" indicate the results from A, B, and C of FIG. 6, respectively. As shown in FIG. 8, the ethamsylate treatment group had a remarkably reduced g-ratio compared to the MTZ treatment group, indicating that the myelin layer of axons became significantly thicker in the ethamsylate treatment group. As shown in FIGS. 6 and 8, the damaged or demyelinated nerve cells in the central nervous system of the zebrafish incubated in the presence of MTZ were regenerated or remyelinated with a significantly higher efficiency when incubated in the presence of ethamsylate than the other cases.

As described above in the embodiments above, according to the one or more embodiments, a composition for preventing or treating a disease associated with demyelination of a nerve cell in a mammal may prevent or treat the disease associated with demyelination of nerve cells in the mammal. A composition for promoting remyelination or suppressing demyelination of nerve cells in a mammal, as described in the embodiments above, may promote remyelination or suppress demyelination of nerve cells in a mammal. A composition for reducing expression of PMP22 in a nerve cell of a mammal, as described in the embodiments above, may reduce expression of PMP22 in nerve cells of a mammal. A method of preventing or treating a disease associated with demyelination in nerve cells of a mammal, as described in the embodiments above, may efficiently prevent or treat a disease associated with demyelination in nerve cells of the mammal. A method of promoting remyelination or suppressing demyelination in nerve cells of a mammal, as described in the embodiments above, may efficiently promote remyelination or suppress demyelination in nerve cells of the mammal. A method of reducing expression of PMP22 in nerve cells of a mammal, as described in the embodiments above, may reduce expression of PMP22 in the nerve cells of the mammal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a disease associated with demyelination of a nerve cell of a mammal, the method comprising administering an effective amount of 2,5-dihydroxybenzenesulfonic acid or a pharmaceutically acceptable salt or solvate thereof to the mammal, wherein the mammal has a disease associated with demyelination of nerve cells.

2. The method of claim 1, wherein the mammal overexpresses PMP22.

3. The method of claim 1, wherein the disease is a disease associated with overexpression of PMP22.

4. The method of claim 1, wherein the disease is multiple sclerosis, Guillain-Barre syndrome, Charcot Marie Tooth (CMT) disease, Dejerine-Sottas disease, or hereditary neuropathy with liability to pressure palsy (HNPP).

5. The method of claim 1, wherein the disease is Charcot Marie Tooth (CMT) subtype CMT1A, CMT1E, or CMT3.

6. The method of claim 1, wherein the method comprises administering a pharmaceutically acceptable salt of 2,5-dihydroxybenzene sulfonic acid.

7. A method of reducing expression of PMP22 in a nerve cell of a mammal with a disease associated with demyelination of a nerve cell, the method comprising administering an effective amount of 2,5-dihydroxybenzenesulfonic acid or a pharmaceutically acceptable salt or solvate thereof to the mammal to thereby reduce expression of PMP22 in the nerve cell of the mammal.

* * * * *